United States Patent [19]
Varki et al.

[11] Patent Number: 5,449,781
[45] Date of Patent: Sep. 12, 1995

[54] FLUORESCENT OR UV VIZUALIZABLE TAGGING AGENTS FOR OLIGOSACCHARIDES

[75] Inventors: Ajit Varki, Del Mar; Barry E. Rothenberg, San Diego, both of Calif.

[73] Assignee: The Regents of the University of California, Oakland, Calif.

[21] Appl. No.: 71,524

[22] Filed: Jun. 2, 1993

[51] Int. Cl.[6] .................. C07D 495/04; A61K 39/44; C07K 1/10

[52] U.S. Cl. .................................. 546/271; 530/367; 435/7.5

[58] Field of Search ........................................ 546/271

[56] References Cited

PUBLICATIONS

Orchin et al, The Vocabulary of Organic Chemistry, Wiley-Interscience publishers, 1980.
Reexamination of the Pyridylamination Used for Fluorescence Labeling of Oligosaccharides and Its Application to Glycoproteins Hase, et al., *J. Biochem.*, No. 1, 95:197–203, 1984.
Improved Method for Fluorescence Labeling of Sugar Chains with Sialic Acid Residues Kondo, et al., *Agric. Biol. Chem.*, No. 8, 54:2169–2170, 1990.
Characterization of Carbohydrate-Binding Specificity of Concanavalin A by Competitive Binding of Pyridylamino Sugar Chains Mega, et al., *J. Biochem.*, 111:396–400, 1992.
Separation of Oligomannose-Type Sugar Chains Having One to Five Mannose Residues by High-Performance Liquid Chromatography as Their Pyridylamino . . . Oku, et al., *Analytical Biochemistry*, 185:331–334, 1990.
Assay of Urinary Free Fucose by Fluorescence Labeling and High-Performance Liquid Chromatography Suzuk, et al., *Clin. Chem.*, No. 5, 38:752–755, 1992.
Hase, et al., J. Biochem., 95:197,203, 1984. Reexamination of the pyridylamination used for fluorescence labeling of oligosaccharides and its application to glycoproteins. Tokyo, Japan.

Primary Examiner—Alan L. Rotman
Attorney, Agent, or Firm—Fish & Richardson

[57] ABSTRACT

Fluorescent tagging compounds of the formula:

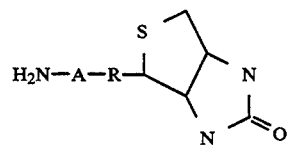

wherein A is a member selected from the group consisting of an aromatic ring, a heteroaromatic ring, and a heterocyclic ring, and R is a linking moiety having from 1 to 20 carbon atoms, optionally containing nitrogen atoms, sulfur atoms, oxygen atoms, carbonyl groups, carboxyl groups, and/or amide groups, as well as fluorescent tagged oligosaccharide adducts derived therefrom are disclosed.

2 Claims, 3 Drawing Sheets

FLUORESCENT OR UV VIZUALIZABLE TAGGING AGENTS FOR OLIGOSACCHARIDES

This invention was partially supported by grant Number RO1CA38701 from the United States Public Health Service. The U.S. Government may have significant rights in this invention.

BACKGROUND OF THE INVENTION

1. Field of the Invention

This invention relates to novel fluorescent tagging agents. More specifically, this invention relates to novel fluorescent tagging agents capable of tagging oilgosaccharides to form oligosaccharide-biotin adducts useful in analytical, diagnostic, and therapeutic application.

2. Description of Related Art

Many of the important biological roles of oligosaccharides involve their interaction with specific receptor proteins. Studies of these interactions require specific oligosaccharides from various biological sources. Isolation of oligosaccharides in individually, structurally definable units is critical to such studies. For the fractionation and detection of oligosaccharides, currently available methods include metabolic labelling, chemical labelling, and high pH anion exchange chromatography with pulse-amperometric detection, all of which are fraught with some problems.

An alternative approach is the tagging of free oligosaccharides by reductive amination with amino-phospholipids or with neutral or acidic fluorescent reagents. Although this approach is useful and practical in some applications, fractionation of the tagged oligosaccharides has certain limitations. Additionally, the fractionated, purified oligosaccharides so obtained are of limited use for purposes other than structural analysis. The only exception is phospholipid tagging, which allows probing of TLC plates by purified receptors that are already known to recognize oligosaccharides. However, these lipid adducts cannot be used as soluble reagents to probe natural or recombinant sources for previously unknown oligosaccharide receptors. Several alternative approaches are available for the probing of oligosaccharide receptors. Neoglycoproteins can be prepared by coupling of defined, unmodified oligosaccharides to proteins such as bovine serum albumin. Neoglycoproteins are used as probe tools with target specificity to cells. Also, oligosaccharides or glycopeptides can be coupled to biotin, resulting in the formation of tight complexes with avidin or streptavidin. The latter approach can utilize the wellknown avidin-biotin technology (Wilcheck, M.; Bayer, E. A., *Anal. Biochem.* 1988, 171, 1-32). However, both approaches suffer from some drawbacks: the neoglycoprotein approach is limited by heterogenous stoichiometry and arrangement of the coupled oligosaccharides on the protein which cannot be controlled; and the biotin approach requires that the oligosaccharide or glycopeptide be first purified to homogeneity, prior to coupling.

In the area of immunology, it has always been problematic to produce a meaningful immune response to carbohydrate antigens. Typically, the immune response which does occur is in the form of a low-affinity IgM, probably due to the fact that antibody responses to sugar chains are T-cell dependent. In addition to low affinity, the IgM produced in response to carbohydrate antigens is often subject to non-specific cross-reactivity with related compounds. In trying to produce a higher affinity IgG response to carbohydrate antigens, researchers have typically resorted to covalent coupling of the carbohydrate antigen to a carrier, such as a foreign protein. However, this latter technique is somewhat laborious and often requires tedious absorption steps to remove antibodies produced in response to the carrier. Thus, considerable need exists for a routine technique which would allow immunogenic presentation of an individual oligosaccharide and purification of oligosaccharide specific immunoglobulin.

Accordingly, there is a long-felt need for a tagging agent for purposes of tagging and fractionating oligosaccharides which allows further application of the tagged, fractionated oligosaccharides. This invention disclosed herein enables the synthesis of novel fluorescent tagging compounds and fluorescent tagged oligosaccharide adducts that possess many desirable properties.

SUMMARY OF THE INVENTION

The fluorescent tagging compounds of this invention comprises an aminoaryl or aminoheteroaryl ring, a biotin moiety, and an elongatable linker arm, which covalently couples the foregoing two moieties.

Thus, the fluorescent tagging compound is represented generally by the structure:

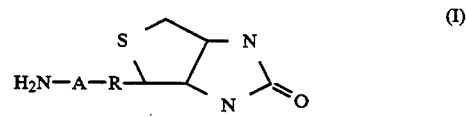

(I)

wherein A is a member selected from the group consisting of an aromatic ring, a heteroaromatic ring, and a heterocyclic ring, and R is a linking moiety having from 1 to 20 carbon atoms, optionally including nitrogen atoms, sulfur atoms, oxygen atoms, carbonyl groups, carboxyl groups, and/or amide groups.

These tagging compounds can be chemically covalently affixed to the individual molecules of an oligosaccharide. This fluorescent tagged oligosaccharide adduct (Formula II) constitute another aspect of this invention.

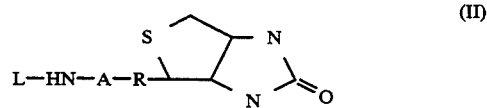

(II)

wherein A and R are as previously defined and L is a residue of an oligosaccharide.

In a third aspect of this invention, this invention provides a process for preparing a fluorescent tagged saccharide adduct of formula (II), which comprises the steps of:

(a) contacting in a medium an oligosaccharide with a fluorescent tagging compound of formula (I), under conditions which are effective to form a Schiff base from the saccharide; and (b) contacting the Schiff base with a reducing agent in a medium.

In a fourth aspect of this invention, particularly favorable complexes are formed when avidin or streptavidin is combined with fluorescent tagged saccharide adducts of formula (II).

In a fifth aspect, this invention provides a method for detecting receptors for a saccharide by using a labeled avidin- or labeled streptavidin-complex of the fluorescent tagged oligosaccharide adduct of formula (II) wherein the oligosaccharide is specific to the receptors.

In a sixth aspect, this invention provides a process for producing monospecific high affinity IgG antibodies directed against oligosaccharides by using an avidin- or streptavidin-complex of the fluorescent tagged oligosaccharide adducts of formula (II).

Additionally, this invention provides a fluorescent tagging compound of the formula (III)

$$HO-A-R-\underset{N}{\overset{S\frown N}{\diagdown/}}=O \quad (III)$$

wherein A and R are as previously defined.

This series of fluorescent tagging compounds can be chemically covalently affixed to a monosaccharide. This fluorescent tagged monosaccharide adduct (Formula IV) is embraced by the present invention $$L-O-A-R-\underset{N}{\overset{S\frown N}{\diagdown/}}=O \quad (IV)$$

wherein A and R are as previously defined and L is a residue of a monosaccharide.

The above objects, as well as further objects, features and advantages of the invention, will be more fully understood by reference to the following detailed description and drawings.

DETAILED DESCRIPTION OF THE INVENTION

Figure 1:
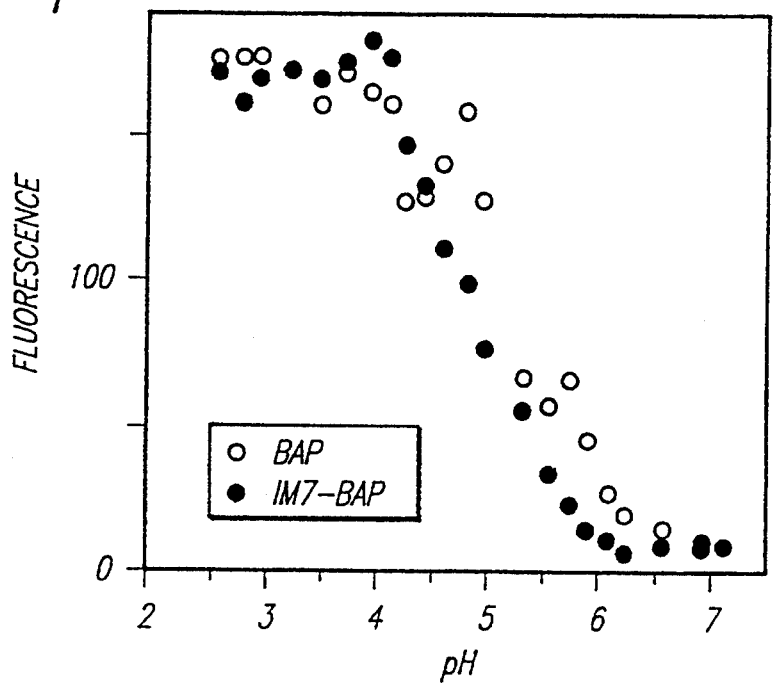
FIG. 1 shows pH dependence of the fluorescence of BAP.

In its broadest aspect, this invention is concerned with a novel method of conjugating a useful oligosaccharide with a fluorescent tag (fluorophore) for analytical, diagnostic application. The invention essentially comprises four parts: fluorescent tagging compounds; oligosaccharide conjugates; avidin- or streptavidin-complex of the oligosaccharide conjugates; and utility of the avidin- or streptavidin complexes.

Preferred embodiments of the invention will follow with each of these parts being described individually.

I. Fluorescent Tagging Compounds

The fluorescent tagging compounds of this invention are represented by the structure set forth in formula (I), wherein A and R are as defined therein.

In formula (I), A can be selected in conjunction with the nature of R so that the fluorescent chromophore of the compound emits fluorescence of suitable intensity for the purpose of fluorescent tagging, and the resulting molecule may not be too hydrophobic to handle.

As used herein, the term "aromatic ring" means $C_6$–$C_{10}$ aryls. The term "heteroaromatic ring" means $C_3$–$C_9$ heteroaryl containing one or more heteroatoms. Preferably, heteroatoms should be oxygen, sulfur or nitrogen. The term "heterocyclic ring" means $C_3$–$C_{14}$ cycloalkyl containing one or more ring heteroatoms.

Preferably, A is a heteroaromatic ring. Especially preferred, A is a pyridine ring.

In formula (I), R can be any group that will serve as a linker without interfering with the fluorescent tag forming ability of the molecule or the binding to avidin or streptavidin. R comprises from 1 to 20 carbon atoms, straight or branched, which further may contain nitrogen atoms, sulfur atoms, oxygen atoms, carbonyl groups, carboxyl groups, and/or amide groups or other groups such as ethers. These groups can also be served as a radical to link the R to the aromatic or heteroaromatic ring. Preferably, R can be optionally substituted alkylenes of from 1 to 10 carbon atoms, arylenes of from 6 to 10 carbon atoms, aralkylenes and alkarylenes of from 7 to 14 carbon atoms. Exemplary R groups include ethylene, n-propylene, isopropylene, n-butylene, and phenylene. Especially preferred R groups are alkylene having 2 to 8 carbon atoms, wherein the alkylene group is terminated with amide. This preferred R group is represented by the formula of —NH—CO—$(CH_2)_n$—, wherein n is an integer of from 2 to 8. Within this group, particularly preferred n value is 4.

In formula (I), the positions of substitution by the R group and by the amino group are not limited, but are preferably in a meta relation to each other. Where A is a pyridine ring, 2-position and 6-position of the ring are preferred for substitution.

For purposes of illustrative clarity and ease of comprehension, only the synthesis of biotinylated aminopyridine (referred to as BAP) is described. This synthesis involves the coupling of diaminopyridine and biotin according to Reaction Scheme 1. It should be understood, however, that the use of these particular exemplary compounds for descriptive purpose shall not restrict nor limit the use or applicability of other compounds and reagents.

$$NH_2\text{-pyridine-}NH_2 \quad (V)$$

$$HOOC(CH_2)_4\text{-biotin} \quad (VI)$$

$$\downarrow EDC, NHS$$

$$NH_2\text{-pyridine-}NH-\overset{O}{\overset{\|}{C}}(CH_2)_4\text{-biotin} \quad (VII)$$

Typically, condensation of diaminopyridine of formula (V with biotin of formula (VI) is conducted in an inert organic solvent at a temperature of from 0° C. to about 100° C. Suitable organic solvents include dimethylformamide (DMF), dimethylsulfoxide (DMSO), hexamethylphosphoamide (HMPA), and MES. Biotin is normally activated prior to reaction with diaminopyridine, involving formation of a symmetric anhydride, mixed anhydride, activated ester, acid chloride or the like. A particularly preferred acid agent used in this invention is N-hydroxysulfosuccinimide (NHS). The activation step can be carried out by various condensing agents, such as carbonyldiimidazole, dicyclohexylcarbodiimide, hydroxybenzotriazole, 1-ethyl-3-(3-dimethylaminopropyl)carbodiimide hydrochloride (EDC) and the like. For each one mole of the biotin, it is necessary to use a 2 to 5 molar excess to avoid formation of a di-biotinqylated adduct. The reaction time varies according to a number of factors, but at about 25° C. reaction times from 0.5 to 24 hours are commonly used. The compound of formula (V) can be isolated and purified by conventional methods known in the art, e.g., chromatography(silica gel, anion exchange) or recrystallization. The structure of compound (VII) can be established by NMR and FAB-MS.

II. Oligosaccharide Conjugates

The oligosaccharides to be conjugated to the fluorescent tagging compound of this invention are those selected to carry out further application such as saccharide receptor detection or antibody production. Any oligosaccharide molecules can be used in this invention as long as the molecule is provided with a functional group available for conjugation. Thus, the oligosaccharide should contain at least one of the groups selected from aldehyde, keto, or hemiacetal, including hemiketal. The most preferred functional group is hemiacetal.

The preferred general procedure for preparing a fluorescent tagged oligosaccharide adduct of formula (II) involves two steps. First, an oligosaccharide is contacted with a fluorescent tagging compound of formula (I) in a medium under conditions which are effective to form a Schiff base. Typical reaction conditions are as follows: about 40–50 fold molar excess of the fluorescent tagging compound such as BAP; the oligosaccharide; buffer (pyridine, glacial acetic acid, 3:1 v/v pH 5.3); 1 hour at 80° C.

The second step involves reduction of the C=N double bond of the Schiff base obtained in the first step. Reduction can be carried out in a number of ways. Reducing agents which can be employed include borane, sodium borohydride, sodium cyanoborohydride, and lithium cyanoborohydride. This reduction is normally conducted at a temperature of from 0° C. to about 100° C., with an excess of the reducing agent in a suitable medium. Conveniently, the reducing agent can be added to the reaction buffer containing the Schiff base. Alternatively, the Schiff base can be reduced with hydrogen. It is normally achieved with a heterogeneous catalyst such as platinum ($PtO_2$), palladium (Pd/C) or nickel in methanol or ethanol at ambient temperature. When the fluorescent tagging compound (I) containing sulfur is converted to a Schiff base, the Schiff base cannot be reduced catalytically, because the sulfur moiety poisons the hydrogenation catalyst. Generally, in selecting the reducing agents and reduction conditions, due care must be given to the liability of saccharide rings. Therefore, the reduction step should be carefully controlled so as not to modify the oligosaccharide. The product of formula (II) can be purified and isolated by conventional means, such as gel filtration and reverse phase high performance liquid chromatography.

In one embodiment, the compound of formula (VII) is coupled with an oligosaccharide to produce a fluorescent BAP-oligosaccharide adduct of formula (VIII) according to the above-indicated process. Reaction is schematically represented by the following:

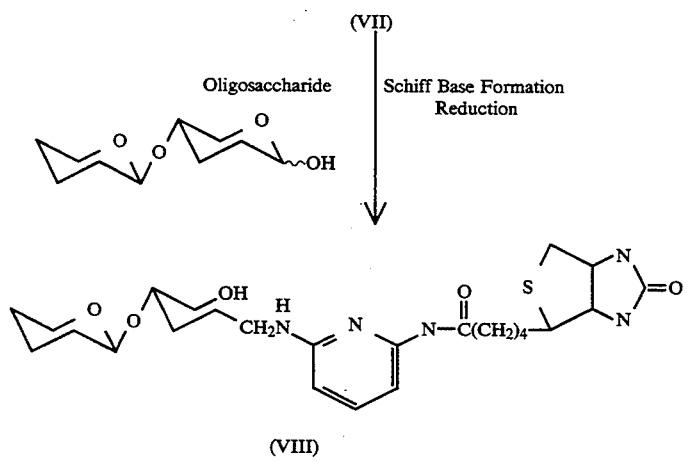

III. Avidin- or streptavidin-complex of the Oligosaccharide Conjugates

The high affinity ($10-15M^{-1}$) interaction between avidin or streptavidin and biotin has been exploited for a wide variety of bioanalytical applications such as affinity chromatography, localization, immunodiagnostics, and detection of nucleic acids.

The avidin- or streptavidin-complex of the fluorescent tagged oligosaccharide (II) can be prepared by standard methods known in the art (e.g., Ohsumi, Y.; Chen, V. J.; Yan, S. B.; Wold, F.; Lee, Y. C., Glycoconjugate J. 1988, 5, 99–106). For example, the fluorescent BAP oligosaccharide of formula (VIII) may be incubated with avidin or streptavidin in a suitable buffer. Following complexation, the product complex may be isolated, purified by the methods known in the art, such as gel-filtration chromatography. Alternatively, the fluorescent BAP oligosaccharide (VIII) may be loaded on affinity column which contains avidin or streptavidin, preferably monovalent avidin or streptavidin. The product complex may be eluted from the column with an appropriate buffer.

Since both avidin and streptavidin are tetravalent for biotin-binding sites, up to four molecules of the fluorescent tagged oligosaccharide adduct of formula (VIII) can be complexed with the glycoprotein. As defined herein, the term "avidin- or streptavidin-complex" encompass complexes which contain more than one molecules of the oligosaccharide.

IV. Utility of the Fluorescent Tagged Oligosaccharide Complexes

Small quantities of the avidin- or streptavidin-complexes of the fluorescent tagged oligosaccharide adduct would be sufficient to produce useful monospecific high affinity IgG antibodies (polyclonal or monoclonal) directed against the saccharides, which in turn could be used to study their expression and tissue distribution.

The avidin- or streptavidin-complexes of the fluorescent tagged oligosaccharide adduct can also be used to detect and study the expression of specific receptors for oligosaccharides in cells and tissues. Further, they could be used to screen recombinant expression libraries for receptor proteins that specifically recognize the oligosaccharides. If an oligosaccharide-specific receptor is discovered in natural or recombinant sources, the fluorescent tagged oligosaccharides could then be used with immobilized avidin or streptavidin to affinity-purify the receptor.

This invention provides a fluorescent tagging compound which offers a versatile approach to the study of oligosaccharides and their biology that combines many of the advantages of previously known techniques and others not achievable by those techniques.

The invention will be further shown by the following Examples. These are intended to amplify the invention and are not to be construed as limiting its scope which is instead defined by the appended claims.

PREPARATION 1

Materials

The preparation of autogalactosylated galactosyltransferase (galT) (Whiteheart, S. W.; Passaniti, A.; Reichner, J. S.; Holt, G. D.; Haltiwanger, R. S.; Hart, G. W.; Methods Enzymol. 1989, 179, 82–94), UDP-[6-$^3$H]Gal (Hayes, B. K.; Varki, A., Anal. Biochem. 1992, 201, 140–145), and PNGase F free of endo F (Plummer, T. H. Jr.; Tarentino, A. L., Glycobiology, 1991, 1,257–263) were as previously described. Isomaltoheptaose (IM-7) was a gift of Dr. Kirsti Granath, Kabi Pharmacia Opthalmics, Sweden. Synthetic Sialyl Lewis$^x$ tetrasaccharide was provided by Drs. Conrad Hummel and K. C. Nicolaou, Scripps Research Institute, La Jolla, Calif. An IgG monoclonal antibody against IM-7 was a gift of Dr. Elvin Kabat, Columbia University, New York, N.Y. Unless otherwise stated, most of the other materials were obtained from Sigma Chemical Company. Sources of other materials are indicated in the description of the individual methods. Preparation of [6-$^3$H]Gal$\beta$1-4GlcNAc$\beta$1-4GlcNAc. A 100 $\mu$l reaction containing 40 mM Chitobiose, 75 $\mu$l 0.2 MSodium Cacodylate pH 6.5, 6 $\mu$l of galT and 30 $\mu$l of UDP-[6-$^3$H]galactose (1 mCi/ml) was incubated at 37° C. for 2 hours, and passed over a 2 ml column of Dowex 1X8 previously equilibrated with 5% w/v sodium tetraborate and prewashed with 10 column volumes of water. The only radioactive species in the run-through and subsequent water washes was [6-$^3$H]Gal$\beta$1-4GlcNAc$\beta$1-4GlcNAc, which was desalted by sequential chromatography on Dowex 3X-4A (free base form) and Dowex 50 (H$^+$ form). The purity of the radioactive product was determined by descending paper chromatography on Whatman #1 paper developed in ethyl acetate:pyridine:acetic acid:water (5:5:1:3).

Preparation of N-linked oligosaccharides from bovine pancreatic RNAse B.

High mannose-type N-linked oligosaccharides from Bovine pancreatic RNAase B were released with PNGase F and purified from the reaction mixture by sequential chromatography on columns of Biobeads SM-2 and Amberlite MB-3 resins. The neutral oligosaccharide mixture passed through both columns in water.

Quantitation

BAP (Example 1) and its oligosaccharide adducts (Example 2) are readily detectable by their fluorescence, especially if the pH is maintained at ~4.0. Measurement and quantitation of the products can be done by standard fluorescence spectrophotmetry, using standardized BAP solutions (as little as 15 pmole can be easily detected in a cuvette holding 1 ml). Using a standard on-line HPLC fluorescence detector, as little as 50 fmole of BAP or a BAP-oligosaccharide can be detected after elution from a standard C18 reverse-phase HPLC column.

Another method of quantitation is a colorimetric assay using competitive binding of biotin with HABA (4'-hydroxyazobenzene-2-carboxylic acid; available from Pierce Chem., Rockford, Ill.). The biotin binding sites of avidin are non-polar and can weakly bind various dyes. When the dye HABA is combined with an excess of avidin, a change in color from yellow to red occurs, and a new absorption band is observed at 500 nm. When biotin is added to the HABA-avidin complex, HABA is quantitatively displaced and the absorption is proportionately decreased. Using a standard curve ~1 nmole or more of BAP covalently bound to an oligosaccharide can be accurately determined. Finally, BAP and its oligosaccharide adducts can also be visualized using a hand held UV light or a UV-light box (pH conditions affect the sensitivity of this detection).

EXAMPLE 2

2-Amino-6-amidobiotinyl-pyridine (BAP)

N-hydroxysulfosuccinimide (NHS), 1-ethyl-3-(3-dimethylaminopropyl) carbodiimide hydrochloride (EDC), and 2,6-diaminopyridine (DAP) were first dissolved in MES, pH 6.5 and biotin (dissolved in DMSO or DMF), added for a 3:1 molar ratio of DAP:biotin. The reaction was allowed to proceed at room temperature for ~1 hour, when a green color appeared, and was then passed over an anion exchange column to remove salts and unreacted biotin. The eluted material was concentrated by lyophilization, dissolved in butanol with heating (95° C.). Once in solution, the mixture was brought to a final concentration of 95% butanol 5% TFA and immediately loaded onto a silica column (Silica gel grade 60, 230–400 mesh, 60 angstroms Merck), equilibrated in 95% butanol and 5% TFA. When the leading fluorescent band (DAP) was halfway down column (monitored with a hand-held UV-light), the running buffer was changed to 85% ethanol. Fractions are collected and analyzed by TLC. All fractions containing BAP were pooled and concentrated at 45° C. on a rotary evaporator with repeated additions of ethanol to remove traces of TFA. The partially purified material was redissolved in 85% ethanol with heating and loaded onto the original silica column, re-equilibrated with 85% ethanol. The product was purified to 100% homogeneity on this column. Final yields of 50% or greater based on the starting biotin were routinely obtained following purification by silica gel chromatography. The title product can be stored in powder form at room temperature or −20° C. in a desiccator. The final product gave a single spot on TLC and a single peak in reverse-phase HPLC analysis.

The synthesis and purification of the title product were monitored by silica gel TLC (DC-Plastikfolien, Kieselgel 60 Art. 5748, Gallade Chemical Inc.) with 85% ethanol. In this system BAP has an Rf of 0.75-0.80, while DAP has an Rf of 0.50. Biotin contamination could be visualized by iodine vapor staining, appearing immediately below the BAP band. BAP was dissolved in methanol (5 μl/μg), and 1 μl loaded onto the LSIMS (liquid secondary ion mass spectrometry) stainless steel target already covered with NBA, and 1 μl of TFE (Trifluoroethanol) was added. The sample was analyzed in the positive ion mode using a VG Analytical 70-SE mass spectrometer fitted with cesium ion gun operated at 25 kV, with an emission current of 2 μA. Mass range 100-1000 was scanned at 25 s/decade, at an ion source accelerating potential of 8 kV, and a resolution of 2,000. Data were acquired and processed on a VG 11-250J data system. The parent peak for the title compound appeared at 336 m.u.

$^1$H-NMR of BAP was recorded at 360 MHz in DMSO-$d_6$ and peak positions are expressed in parts per million (ppm) downfield from tetramethylsilane (Table 1).

TABLE 1

| Proton | J (Hz) | ppm |
|---|---|---|
| H-2$\beta$ | $J_{2\beta,3\beta}$ = 3.6 | 3.05 |
| H-3$\beta$ | $J_{2\beta,\delta}$ = 7.2 | 4.07 |
| H-4$\beta$ | $J_{3\beta,\delta}$ = 3.6 | 4.24 |
| H-5$\alpha$ | $J_{4\beta,5\beta}$ = 7.2 | 2.52 |
| H-5$\beta$ | $J_{5\alpha,5\beta}$ = 10.8 | 2.77 |
| H-$\alpha$ | $J_{\alpha,\beta}$ = 7.2 | 2.32 |
| H-$\beta$ | — | 1.43 |
| H-$\delta$ | — | 1.30 |
| H-$\delta$ | $J_{\delta gem}$ = 14.4  $J_{\delta vec}$ = 7.2 | 1.53 |
| H'-$\delta$ | — | 1.39 |
| H-3'',4'',5'' | — | 6.28 |

Complete spectral analysis gave excitation and emission maxima of 341 nm and 387 nm, respectively. The fluorescence yields are markedly pH-dependent for BAP in ammonium acetate buffer. A pH of 4.1 or less gave the greatest fluorescence yield (FIG. 1).

EXAMPLE 3

Oligosaccharide-BAP Adduct

Oligosaccharides to be reacted with BAP were dissolved in reaction buffer (pyridine:glacial acetic acid, 3:1 v/v pH 5.3). Prior dissolution of the oligosaccharides in a minimal amount of DMSO or water was required for large neutral or acidic oligosaccharides, respectively. Reactions were run in small reaction vial with final volumes varying between 11-100 μl depending on the amount of oligosaccharide and BAP concentration. A 40-50 fold molar excess of BAP was added to the reaction buffer containing the oligosaccharide, capped tightly and placed at 80° C. After 1 hour, an equal volume of reducing agent (25 mg/200 μl of borane-dimethylamine complex) was added and the reaction was allowed to proceed for another hour.

The efficiency of coupling varied somewhat, depending on the oligosaccharides studied. For small neutral chains such as [$^3$H]Gal-chitobiose and isomaltoheptaose (IM7), yields of 75-80% were consistently obtained. Yields for negatively charged molecules, containing 1 or 2 sialic acid residues were slightly less (e.g., ∼65-70% for a biantennary bisialylated N-linked oligosaccharide). In addition, neutral oligosaccharides (e.g., IM7) reacted better when they were first dissolved in minimal volumes of DMSO, whilst reactions with negatively charged oligosaccharides seem to be aided by addition of minimal amounts of water.

Gel Filtration

The coupling reactions are brought up in 0.5 ml with 50% acetonitrile and loaded onto a 85 ml TOYO-PEARL HW40S size separation column equilibrated with 50% acetonitrile, 10 mM sodium acetate. Fractions (0.5-1 ml) were collected and analyzed for fluorescence as described below. Oligosaccharide adducts as small as trisaccharides (e.g., [$^3$H]Gal-chitobiose) eluted earlier than the major peak of residual BAP. Pooled fractions were concentrated on a shaker evaporator and redissolved in dH$_2$O. To separate any unreacted oligosaccharide chains from the oligosaccharide adducts, the pooled fractions were loaded onto a Sep-Pak C18 cartridge, washed with 10 ml dH$_2$O and the oligosaccharide-BAP adducts eluted with 50% acetonitrile. Alternatively, purification was done on LC-NH$_2$ cartridge (binding in >85% acetonitrile, elution with water for neutral oligosaccharides or with phosphate buffer for acidic compounds).

Separation by Reverse Phase-HPLC

Figure 2A:
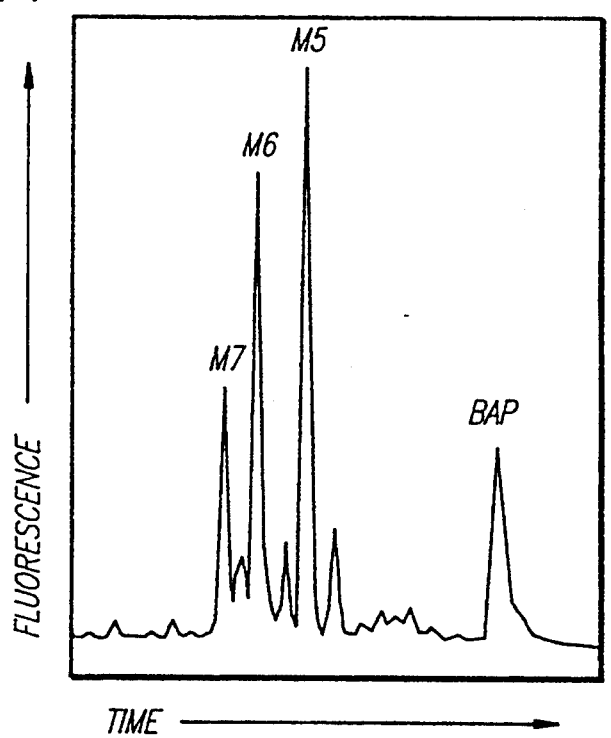
FIG. 2a shows fractionation of BAP-oligosaccharide adducts by RPHPLC.

C$_{18}$ HPLC columns were equilibrated in 10 mM ammonium formate pH 4.1, and samples were loaded in the same buffer. Columns were eluted with linear gradients of acetonitrile against the same buffer, increasing up to the concentration required to elute unmodified BAP (usually ∼25%). The gradients could be adjusted as needed to optimize separation of various compounds. The separation was monitored at excitation and emission maxima of 345 nm and 400 nm, respectively. The fluorescent adducts show excellent peak separation under standard conditions of reverse-phase HPLC (FIG. 2a). FIG. 2a represents BAP adducts of N-linked oligosaccharides from RNAse B. In the figure, M$_5$ is Man$_5$GlcAc$_2$, M$_6$ is Man$_6$GlcNAc$_2$, and M$_7$ is Man$_7$GlcNac$_2$, respectively. BAP is used as an internal standard.

Oligosaccharide Sequencing by Exoglycosidase Digestions

Figure 2B:
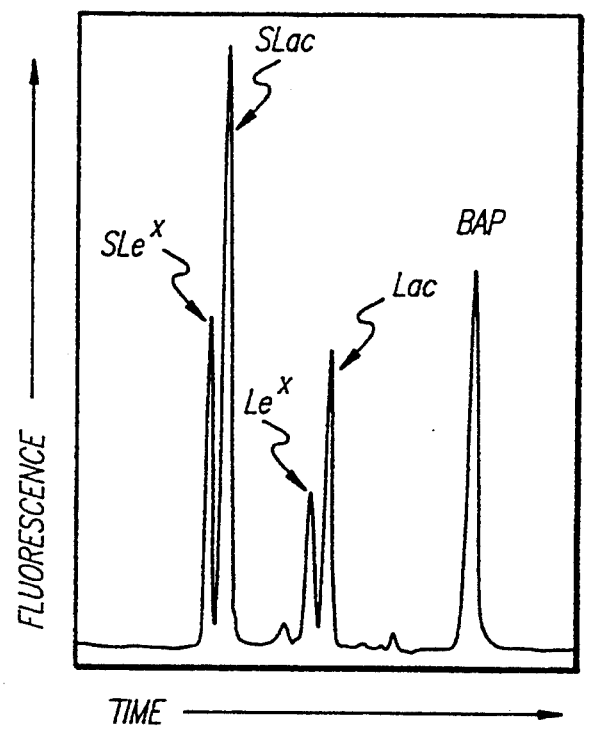
FIG. 2b shows fractionation and sequencing (by exoglycosidases) of BAP-oligosaccharide adduct.

BAP-oligosaccharide adducts were treated with 2 mU Arthrobacter ureafasciens sialidase in 10 mM sodium acetate pH 4.6 for 30 minutes at 37° C. Reactions were heat inactivated by boiling for 3 minutes, spun in a microfuge and the supernate directly loaded onto HPLC column. Removal of a single monosaccharide was sufficient to cause a baseline shift in an oligosaccharide-BAP adduct peak (see FIG. 2b). FIG. 2b represents BAP adducts of sialylactose and Sle$^x$ tetrasaccharide. They Were treated individually, or as mixtures with A. ureafaciens sialidase. In the figure, a mixture of the two is shown after partial digestions. BAP is used as an internal standard. Thus, single, combined or sequential treatment of purified adducts by exoglycosidases should allow sensitive and rapid compositional and sequence analysis of the oligosaccharides. When using oligosaccharide-BAP adducts of known structure, this system could also be used for sensitive detection of contaminating enzymatic activities in exoglycosidase preparations. Also, following the use of endoglycosidases, the release of specific fragments could be monitored following re-derivatization. Thus, for example, treatment of an N-linked oligosaccharide carrying polylactosaminoglycans could be monitored after endo-β-galactosidase digestion by re-derivatization and RP-HPLC; both the shift in elution of the original oligosaccharide adduct and the appearance of new fragments could be quantitated.

Figure 3:
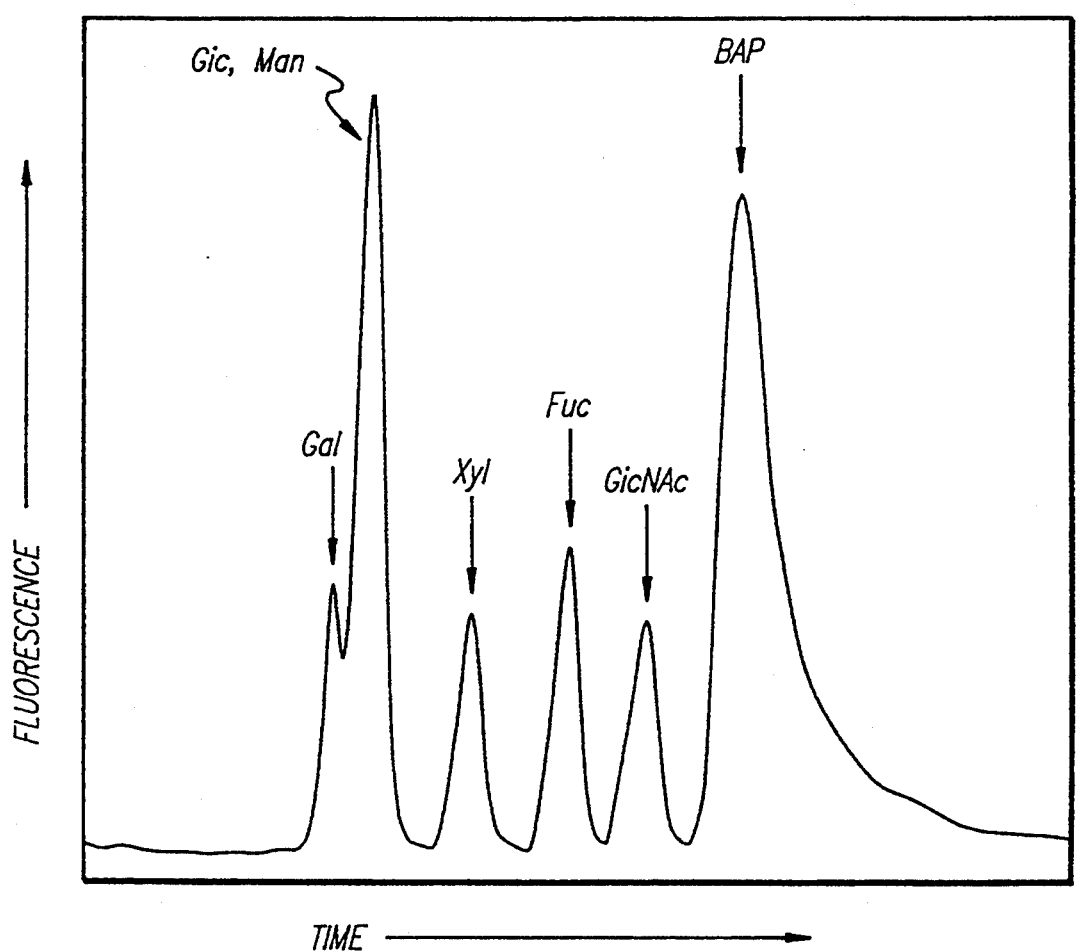
FIG. 3 shows separation of monosaccharide-BAP adducts by RP-HPLC.

Even the BAP-adducts of monosaccharides can be separated by reverse-phase HPLC with little difficulty, using a shallower acetonotrile gradient (see FIG. 3). While this permits partial compositional analysis of oligosaccharides, some monosaccharides are not sufficiently separated from each other (e.g., Gal and Man, see FIG. 3). However, when combined with specific exoglycosidase digestions, this can further facilitate sequencing. Thus, following exoglycosidase digestion of a specific BAP-oligosaccharide adduct, the sample can be rederivatized with BAP and then analyzed by a two-component gradient on RP-HPLC. This would allow the simultaneous detection of a shift in position of the original adduct (in the first part of the gardient) and the detection and quantitation of the released monosaccharide (in the second part of the gradient). In this case, the overlap between certain monosaccharide adducts, e.g., Man-BAP and Gal-BAP, would not be a concern because the nature of the exoglycosidase used (mannosidase or galactosidase) would be known.

EXAMPLE 4

Avidin or Streptavidin Complex of BAP Oligosaccharide Adduct

Rapid re-purification of the oligosaccharide adduct is possible on monovalent avidin columns after various reactions. Elution from monovalent avidin could be done with a volatile buffer (e.g., formate buffer) at pH 2.8, thus permitting removal of salts and reagents from the initial reaction. BAP-oligosaccharide adducts could be recognized with very high affinity by avidin or streptavidin (dissociation constant $\sim 10^{-15}$). The attachment was non-covalent, and could be disrupted by various methods. If a completely saturated (tetravalent) complex is desired, an excess of the adduct is used, and the complex is purified by passage over an iminobiotin column. Any avidin (or streptavidin) that is not fully saturated will bind to this column via the available binding sites, whereas the fully saturated material will run through. The excess of the oligosaccharide can be recovered by gel filtration, or by passage over a monovalent avidin column. The complexes will run through this column, whereas the free adducts will bind and can be recovered by elution at low pH. Partially saturated (monovalent through trivalent) complexes can be prepared by mixing the adducts with the appropriate excess of avidin or streptavidin. The subsequent separation of the complexes into individual species is possible based upon the properties of the oligosaccharide (e.g., charged complexes could be separated by ion exchange chromatography or iso-electric focussing). Once formed and fractionated, the complexes are quite stable because of the low off-rate of the biotin-avidin interaction.

EXAMPLE 5

Production of Polyclonal Antibodies Against BAP-Oligosaccharide Adducts

HPLC-purified IM-7-BAP adducts (3.3 nmol) were coupled to streptavidin, the complexes mixed with complete Freund's adjuvant and injected IP into 16-week old C3H/HeN female mice. One month later, three booster injections were given in incomplete Freund's adjuvant at 2-week intervals. Serial serum samples were obtained by orbital bleeding, prior to and following the immunizations. For screening of IgG antibody production, serum samples were tested in an ELISA assay against the same IM-7 oligosaccharide coupled to BSA by reductive amination (Katzenellenbogen, R. E.; Jennings, H., Can J. Biochem, Cell Biol. 1984, 62, 270-275). Thus, the ELISA assay would detect antibody production against the sugar chain, and not against the streptavidin or BAP present in the immunogen.

Figure 4:
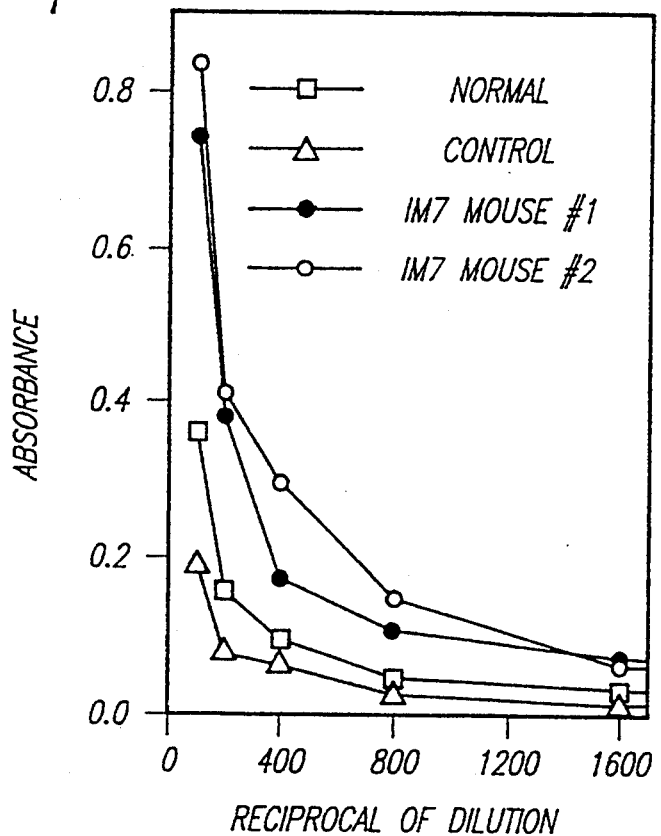
FIG. 4 shows production of specific IgG antibody responses against oligosaccharides using BAP-oligosaccharide adducts complexed with streptavidin.

As shown in FIG. 4, when coupled to streptavidin, IM-7 BAP adduct generated specific IgG antibodies directed against the oligosaccharide. In principle, this approach could be applicable to any oligosaccharide that can be coupled to BAP in low ug quantities. Also, the spleens of such immunized mice should allow the generation of high-affinity monospecific IgG monoclonal antibodies directed against the oligosaccharide of interest.

EXAMPLE 6

Detection of the Mannose Receptor On Mouse Bone Marrow Macrophages $[^{35}S]$Streptavidin is saturated with BAP-coupled RNAase-B high mannose-type N-linked oligosaccharides (saturation can be proven by the lack of ability of the complex to binding to an iminobiotin column). Mouse bone marrow macrophages are cultivated as previously described and plated on 6-well plates. The $[^{35}S]$streptavidin complex is allowed to bind to the surface of the cells at 4° C., wherein endocytosis cannot occur. After a sufficient period of time, the supernatant is removed, the cells washed once with HBSS, and the bound radioactivity determined. The specificity pf binding is determined with either BlcNAc-BAP (nonbinding) or by specific inhibition with 25 mM alphamethyl mannoside.

EXAMPLE 7

Fluorescent Tagged Monosaccharide Adducts

Monosaccharide adducts of formula (III) can be prepared by coupling of suitably protected glycosyl halide derivatives with 2-hydroxy-6-amidobiotinylpyridine. Representative monosaccharides are GalNAc and GlcNAc. The stereochemical outcome of the reactions can be controlled via the 2-substituent of the glycosyl halide, giving the α- or β-glycoside. For the α-product, a non-neighboring group active substituent such as a O-benzyl or azido group will be utilized. For the β-product, neighboring group active substituents such as N-pthalimido or O-acette will be used. The resultant copled products will be converted into the desired unprotected tethered monosacharides via chemical transformations known to one skilled in the art. The final products will be characterized by NMR and mass spectrometry. These compounds will be added to metaboically labelled tissue culture cell These compounds will be added to metaboically labelled tissue culture cell lines known to express the O-linked oligosaccharides of interest. The resulting glycoside chains secreted into the medium will be isolated by reverse-phase chromatography and further purified if necessary by avidin-sepharose affinity chromatography. The resulting "libraries" of oligosaccharides will be fractionated by reverse-phase HPLC, first at the analytical level. If the results appar promising, the preparation will be scaled up, and large-scale purification will be carried out. The fractionated oligosaccharides will be structurally characterized by proton NMR, serial exoglycosidase digestions, methylation analysis with gas-liquid chromatography/mass spectrometry, and (if necessary) FAB-mass spectrometry.

The invention now being fully described, it will be apparent to one of ordinary skill in the art that many changes and modifications can be made without departing from the spirit or scope of the invention.

We claim:

1. A fluorescent or UV visualizable tagging compound of the formula:

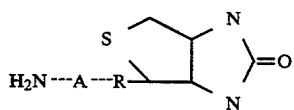

wherein A is a member selected from the group consisting of pyridine and benzamide, and R is a linking moiety —NHCO—[CH$_2$]$_n$ wherein n is an integer from 2 to 8 and wherein the compound is fluorescent or UV visualizable.

2. A compound of claim 1 wherein A is selected from the group consisting of 2,6 and 3,5 pyridine and 2,6 and 3,5 benzamide.

* * * * *